(12) United States Patent
Govaerts et al.

(10) Patent No.: US 9,913,621 B2
(45) Date of Patent: Mar. 13, 2018

(54) METHOD FOR ACCURATELY GENERATING A RADIATION IMAGE OF A REGION OF INTEREST

(71) Applicant: Agfa HealthCare NV, Mortsel (BE)

(72) Inventors: Wim Govaerts, Mortsel (BE); Yves Vanmeenen, Mortsel (BE); Danny Janssens, Mortsel (BE)

(73) Assignee: Agfa HealthCare NV, Mortsel (BE)

( * ) Notice: Subject to any disclaimer, the term of this patent is extended or adjusted under 35 U.S.C. 154(b) by 205 days.

(21) Appl. No.: 14/761,727

(22) PCT Filed: Feb. 3, 2014

(86) PCT No.: PCT/EP2014/052052
§ 371 (c)(1),
(2) Date: Jul. 17, 2015

(87) PCT Pub. No.: WO2014/118369
PCT Pub. Date: Aug. 7, 2014

(65) Prior Publication Data
US 2015/0359494 A1    Dec. 17, 2015

Related U.S. Application Data

(60) Provisional application No. 61/760,667, filed on Feb. 5, 2013.

(30) Foreign Application Priority Data

Feb. 4, 2013 (EP) ..................................... 13153826

(51) Int. Cl.
*A61B 6/08* (2006.01)
*A61B 6/06* (2006.01)
*A61B 6/00* (2006.01)

(52) U.S. Cl.
CPC .................. *A61B 6/08* (2013.01); *A61B 6/06* (2013.01); *A61B 6/4233* (2013.01);
(Continued)

(58) Field of Classification Search
CPC ........... A61B 6/00; A61B 6/08; A61B 6/4291; A61B 6/547; G01N 23/04; G01N 23/08;
(Continued)

(56) References Cited

U.S. PATENT DOCUMENTS 6,097,833 A     8/2000  Lobregt et al.
6,944,265 B2 *  9/2005  Warp .................. A61B 6/4233
                                                        378/116
(Continued)

FOREIGN PATENT DOCUMENTS

EP    2 497 424 A1   9/2012
GB    2 433 668 A    6/2007
WO    2012/147122 A1 11/2012

OTHER PUBLICATIONS

Official Communication issued in International Patent Application No. PCT/EP2014/052052, dated Apr. 3, 2014.

*Primary Examiner* — Jurie Yun
(74) *Attorney, Agent, or Firm* — Keating and Bennett, LLP

(57) ABSTRACT

An offset of an actual positional relationship of a radiation source and an object from a reference positional relationship is determined and taken into account when positioning and/or tilting and/or collimating the radiation source so as to irradiate a region of interest of the object.

6 Claims, 2 Drawing Sheets

(52) U.S. Cl.
CPC ............ *A61B 6/4291* (2013.01); *A61B 6/505* (2013.01); *A61B 6/5241* (2013.01); *A61B 6/547* (2013.01)

(58) Field of Classification Search
CPC .. G01N 23/083; G01T 1/2928; G03B 42/047; A61N 5/1049
USPC ..... 378/62, 98.8, 98.12, 154, 163, 164, 205, 378/206
See application file for complete search history.

(56) References Cited

U.S. PATENT DOCUMENTS

| | | |
|---|---|---|
| 2002/0081010 A1* | 6/2002 | Chang ................. A61B 6/5241 382/132 |
| 2004/0105526 A1 | 6/2004 | Zhang et al. |
| 2009/0207971 A1 | 8/2009 | Uhde et al. |
| 2012/0039447 A1 | 2/2012 | Lalena et al. |
| 2012/0307965 A1 | 12/2012 | Bothorel et al. |

* cited by examiner

METHOD FOR ACCURATELY GENERATING A RADIATION IMAGE OF A REGION OF INTEREST

CROSS-REFERENCE TO RELATED APPLICATIONS

This application is a 371 National Stage Application of PCT/EP2014/052052, filed Feb. 3, 2014. This application claims the benefit of U.S. Provisional Application No. 61/760,667, filed Feb. 5, 2013, which is incorporated by reference herein in its entirety. In addition, this application claims the benefit of European Application No. 13153826.6, filed Feb. 4, 2013, which is also incorporated by reference herein in its entirety.

BACKGROUND OF THE INVENTION

1. Field of the Invention

The present invention relates to a method of recording a radiation image of a region of interest of an object. The present invention is applicable in a method for composing a radiation image of a long length object by radiation images of parts of the long length object and for accurately locating each of these parts of the long length object.

2. Description of the Related Art

In X-ray radiography an x-ray image of a long length object (also called elongate object), such as the entire spine or the legs of a patient, may have to be obtained.

In Computed Radiography (CR), such a long length image is generated by simultaneously subjecting a number of Imaging Plates (IP), such as photo-stimulable phosphor plates, which are organized in a partially overlapping disposition to an x-ray image of the long length object. Each of the imaging plates carries an image of a part of the long length object. After exposure, the individual imaging plates are read out so as to obtain partial images of the long length object and finally a long length image is created by stitching these partial images. Accurate alignment and measurement can be obtained by superimposing a grid of radiation attenuating material covering the region to be imaged and correcting and aligning the partial images to reconstruct the geometry of said grid.

In recent years, Digital Radiography (DR) has become a valuable alternative for CR. The flat panel detectors (FPD) used in DR are more costly than the IP's for CR, so an alternative to the one-shot long length imaging technique of CR using multiple Imaging Plates is needed. This is achieved by taking plural partial images of a long length object by moving the position of the FPD while tilting the X-ray tube and/or moving the X-ray tube parallel to the FPD and/or collimating.

In one embodiment a method for positioning the x-ray source for the generation of the different partial images generally consists of the following steps:
- determining the total length of said long length object to be imaged,
- calculating on the basis of said determined length and (a) predefined amount(s) of overlap between the partial images, the number of partial images required to image said long length object,
- determining on the basis of the calculated number of partial images, the size and position of said partial images, to cover the long length object,
- consecutively exposing parts of the long length object to generate partial images,
- detecting partial images by a radiation detector and reading out said partial images and
- pasting said partial images to form said image of said long length object.

In order to be able to paste the partial images so as to make a correct reconstruction of the entire long length image, an object of known geometric dimensions, e.g. a grid consisting of wires of x-ray attenuating material or a grid comprising x-ray attenuating markers at known positions, is positioned together with the long length object in the beam of radiation so that the radiation image of each time another part of the object of known dimensions (e.g. a grid) appears superposed on each of the partial images. By reconstructing the image of the entire grid, the partial images of the long length object can accurately be recomposed to form the complete radiation image of the long length object.

In order to record the partial images, the source of x-rays has to be positioned and occasionally tilted and collimated so that the emitted beam of radiation successively irradiates the different juxtaposed or slightly overlapping parts of the long length image.

This is achieved via parameters (coordinate) settings applied to a controlling device controlling the positioning and/or tilting and/or collimation of the radiation source.

However, adjustment inaccuracies might occur when adjusting the settings of the x-ray source. Specifically in applications in which a long length object is exposed when it is in a horizontal position on a supporting table, it might occur that the relative position of the supporting table and/or of the grid used for reconstructing the long length image from the partial images is unknown or has changed with respect to an expected position. This might be due to the fact that the table and/or grid may have shifted in the horizontal direction and may thus have been displaced relative to the source position.

This might cause an inaccurate setting of the x-ray source.

SUMMARY OF THE INVENTION

It is an object of the present invention to overcome the above-described problems.

The above-mentioned aspect is obtained by a method and a system as described below. Specific features for preferred embodiments of the invention are also set out below.

Further advantages and embodiments of the present invention will become apparent from the following description and drawings.

DETAILED DESCRIPTION OF THE PREFERRED EMBODIMENTS

The present invention will be explained hereafter for specific embodiments in which a radiation image of a long length object is obtained by combining partial radiation images pertaining to image parts of the long length object that together form the radiation image of the total long length object.

It will be clear that the same method and system can be applied in case of the irradiation of a region of interest on a object of normal (non-long length) dimensions, i.e. an image that can be recorded on a single radiation detector in a single exposure step.

X-ray systems capable of performing long length imaging are available in different configurations, each controlled differently to obtain optimal results for long length imaging. Common parts of the configurations are: an X-ray generation unit including an X-ray source that generates x-rays; a collimator unit which is adjustable and reduces the area on which X-rays are projected; an X-ray imaging unit capable of collecting images based on the generated X-rays.

Most modern systems include controllers to control the X-ray generation unit and X-ray imaging unit. Automatic systems, needed to perform automatic long length imaging, also include position mechanisms and controllers for the positions of the X-ray generation and X-ray imaging unit. In systems such as a C-Arm or U-Arm, some mechanisms and controllers are combined. These position mechanisms and controllers adjust settings of the x-ray source (position, tilt and collimation) on the basis of information on the location of the region of interest to be irradiated (e.g. coordinates) input into these controllers.

Figure 1:
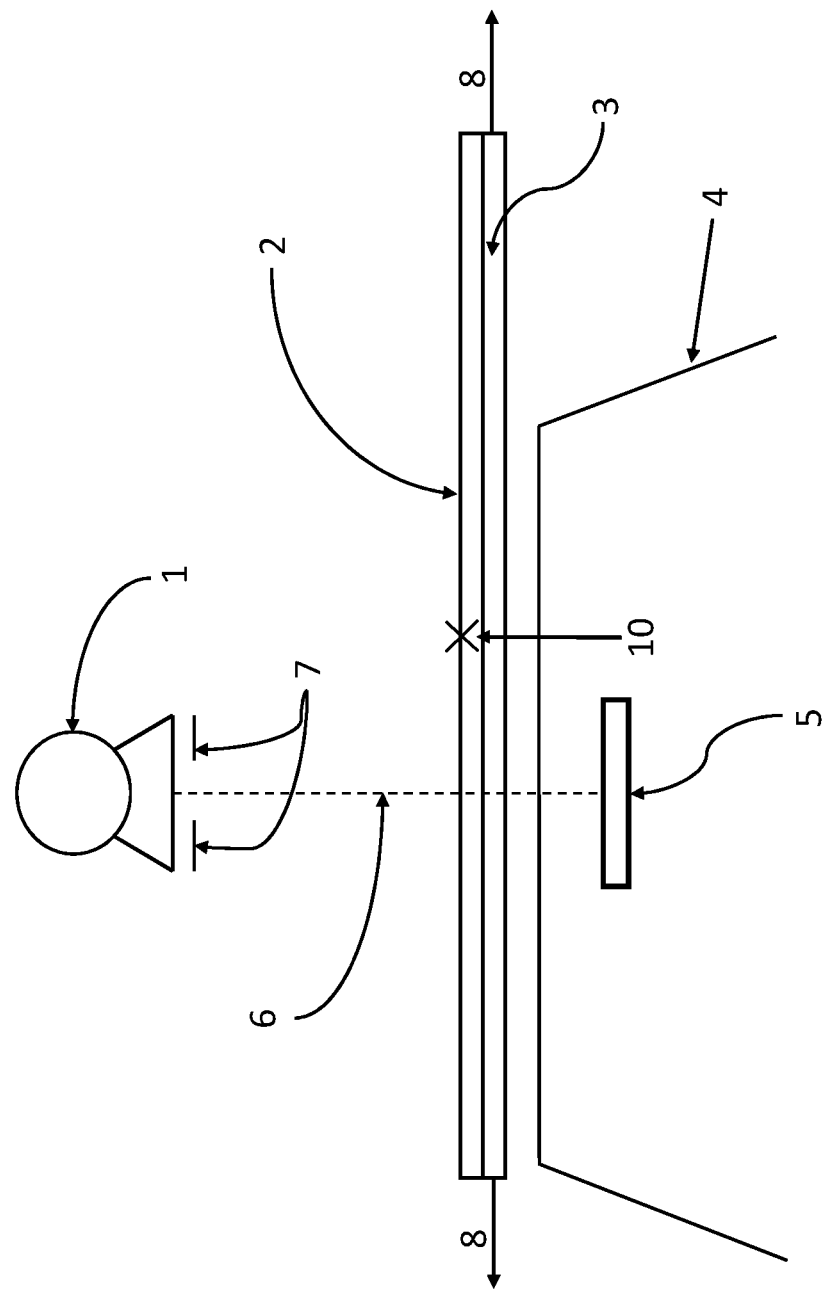
FIG. 1 illustrates the relative positioning of the x-ray source and a table supporting an object to be irradiated.

FIG. 1 schematically shows a source of X-rays (1) projecting a beam of x-rays on a supporting table (2) which is movable in a horizontal plane in both directions indicated by arrows (8) and (9).

A long length object e.g. a leg or spine of a patient and a grid of x-ray attenuating material (3) is positioned on a supporting table (3) that can be displaced in horizontal direction (8,9). By adequately setting the position and/or tilt and/or collimation (by collimator 7) of the source of radiation and then energizing the source of radiation, partial radiation images of the long length object are generated by multiple shot irradiation and read out of a direct radiography detector.

During irradiation a grid of x-ray attenuating material is present in the beam of x-rays together with the long length object so that the partial images comprise partial images of the grid on top of partial images of the long length object. The partial images of the grid can be used to reconstruct the total grid image, whereby automatically also an accurate re-composed image of the long length object is obtained. Use of a grid to reconstruct an image of a long length object from partial images is known in the art and is for example described in published European patent application EP 2 497 424.

Instead of a grid of X-ray attenuating material other embodiments could also be used such as an assembly of x-ray attenuating markers, object part markers etc.

The radiation source must be accurately positioned for sequential irradiation of each of the parts of the long length object and grid so as to generate the above described partial images.

In order to be positioned correctly, coordinate data on the borders of the part of the long length image to be irradiated or of a region of interest to be irradiated are input into a controlling device which controls the settings of the x-ray source, i.a. the position and/or tilt and/or collimation of the x-ray source. These data are determined relative to a reference position. The reference position in case of horizontal positioning of the long length object, is a position of the x-ray source relative to the table supporting the long length body. Alternatives may be envisaged.

However, in case the position of the table would change, the position of the source relative to this reference position would also change, implying that the positioning and tilt of the source set for irradiation of a region of interest on the long length object might be incorrect.

According to preferred embodiments of the invention this problem is solved by generating an indication of the actual position (at the recording a radiation image) of the source relative to the long length object or relative to a support supporting the long length object and by determining the offset of this actual position from a reference position. This offset is then taken into account when determining the required source position, tilt and collimation requirements for generating a radiation image of a region of interest, e.g. a partial radiation image of the long length object.

Figure 2:
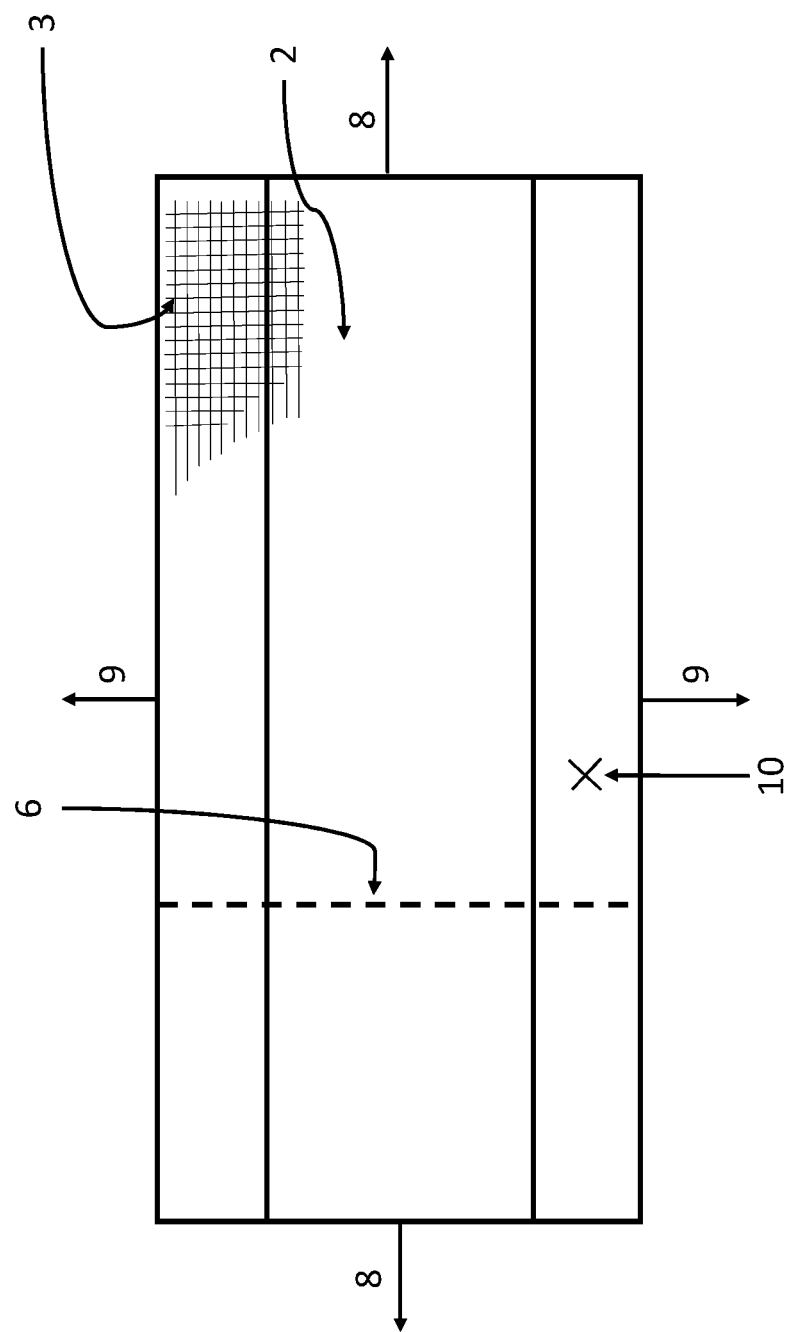
FIG. 2 is a top view illustrating the position of the x-ray source relative to a region of interest.

In one embodiment of the present invention, as illustrated in FIGS. 1 and 2, this is performed by detecting and registering the perpendicular projection (6) on the table of light originating from the x-ray source. If the table is then provided with (a) marker(s) (10) indicative of a reference position, the position relative to the x-ray source is known, the offset of the projected light relative to the reference position can be determined and this deviation can be taken into account when identifying the borders of a region of interest. These data on the location of the borders can be used when setting the position and tilt and collimation of the source of radiation so that it irradiates the envisaged region of interest.

The actual position of the x-ray source relative to the long length object (or to a supporting table) can be determined in several ways. Examples of means for determining this actual position are visual or non-visual light. However, any other means able to provide an indication of the location of the source may be envisaged such as mechanical position determining means, e.g. a vertical ruler positioned between source and object perpendicular to the plane of the object.

Once the offset is known, the actual position of the borders of the region of interest (which can be the entire long length object or a part of this object) can be determined and entered into a system for calculating the positions of the partial images which together form the entire image of the long length object. Methods for calculating the number of these images and for calculating the borders of such images are known in the art and are for example described in the published European patent application 2 508 132.

Having described in detail preferred embodiments of the current invention, it will now be apparent to those skilled in the art that numerous modifications can be made therein without departing from the scope of the invention as defined in the appending claims.

The invention claimed is:

1. A method for generating a radiation image of a region of interest of an elongated object on a supporting table, the radiation image including a plurality of partial radiation images each being obtained by irradiating a portion of the elongated object, the method comprising the steps of:
   determining an offset between an actual position of a radiation source and a reference position on the supporting table by projecting light, perpendicular to the supporting table, from the actual position of the radiation source onto the supporting table, and measuring a deviation between a position of the light projected on the supporting table and a radiation attenuating marker indicating the reference position;
   determining settings of the radiation source to irradiate the plurality of partial radiation images by taking into account the offset;
   positioning the radiation source according to the settings; and irradiating the elongated object to generate the plurality of partial radiation images.

2. The method according to claim 1, further comprising the step of recording the radiation image on a direct radiography detector.

3. The method according to claim 1, further comprising the step of irradiating a radiation attenuating grid at known positions in combination with the elongated object.

4. The method according to claim 3, wherein the radiation image of the elongated object is obtained by recombining the plurality of partial radiation images including a partial image of the elongated object and a partial image of the radiation attenuating grid so that the radiation image of a complete grid is reconstructed.

5. The method according to claim 3, wherein the radiation attenuating grid includes a ruler to determine a position of the elongated object and borders of the region of interest.

6. A system for recording a radiation image of a region of interest of an elongated object on a supporting table, the radiation image including a plurality of partial radiation images each being obtained by irradiating a portion of the elongated object, the system comprising:

a radiation source configured to irradiate the elongated object;

a supporting table including at least one radiation attenuating marker;

means for identifying an offset between an actual position of the radiation source and a reference position on the supporting table by projecting light, perpendicular to the supporting table, from the actual position of the radiation source onto the supporting table, and measuring a deviation between a position of the light projected on the supporting table and the at least one radiation attenuating marker indicating the reference position;

means for determining settings for the radiation source to irradiate the region of interest by taking into account the offset; and means for positioning the radiation source according to the settings.

* * * * *